United States Patent [19]

Morimoto et al.

[11] Patent Number: 4,578,259

[45] Date of Patent: Mar. 25, 1986

[54] PROCESS FOR PREPARING A CRYSTALLINE ALUMINOSILICATE

[75] Inventors: Nobuyuki Morimoto; Kozo Takatsu, both of Sodegaura; Michio Sugimoto, Ichihara, all of Japan

[73] Assignee: Research Association for Petroleum Alternatives Development, Tokyo, Japan

[21] Appl. No.: 582,529

[22] Filed: Feb. 22, 1984

[30] Foreign Application Priority Data

Mar. 7, 1983 [JP] Japan ................................. 58-35926
Oct. 14, 1983 [JP] Japan ............................... 58-190977

[51] Int. Cl.$^4$ ............................................. C01B 33/28
[52] U.S. Cl. .................................... 423/329; 423/328; 502/77
[58] Field of Search .................. 423/326, 328, 329; 502/60, 62, 77

[56] References Cited

U.S. PATENT DOCUMENTS

| | | | |
|---|---|---|---|
| 4,000,248 | 12/1976 | Martin | 423/329 |
| 4,016,245 | 4/1977 | Plank et al. | 423/328 |
| 4,205,053 | 5/1980 | Rollmann et al. | 423/328 |
| 4,251,499 | 2/1981 | Nanne et al. | 423/329 |
| 4,377,502 | 3/1983 | Klotz | 423/329 X |
| 4,390,457 | 6/1983 | Klotz | 423/328 X |

*Primary Examiner*—Edward J. Meros
*Attorney, Agent, or Firm*—Frishauf, Holtz, Goodman & Woodward

[57] ABSTRACT

Crystalline aluminosilicates, a process for the production thereof and uses therefor are disclosed. The crystalline aluminosilicates are of new crystalline structure, which, as determined after calcination in the air at 550° C., have a composition represented by the general formula (I):

$$pM_{2/n}O \cdot Al_2O_3 \cdot qSiO_2$$

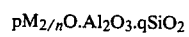

(the symbols are as defined in the appended claims) and give a principal X-ray diffraction pattern as shown in Table 1. They are used as catalysts for the conversion of synthesis gas or oxygen-containing organic compounds such as alcohol, ether into hydrocarbons.

1 Claim, 1 Drawing Figure

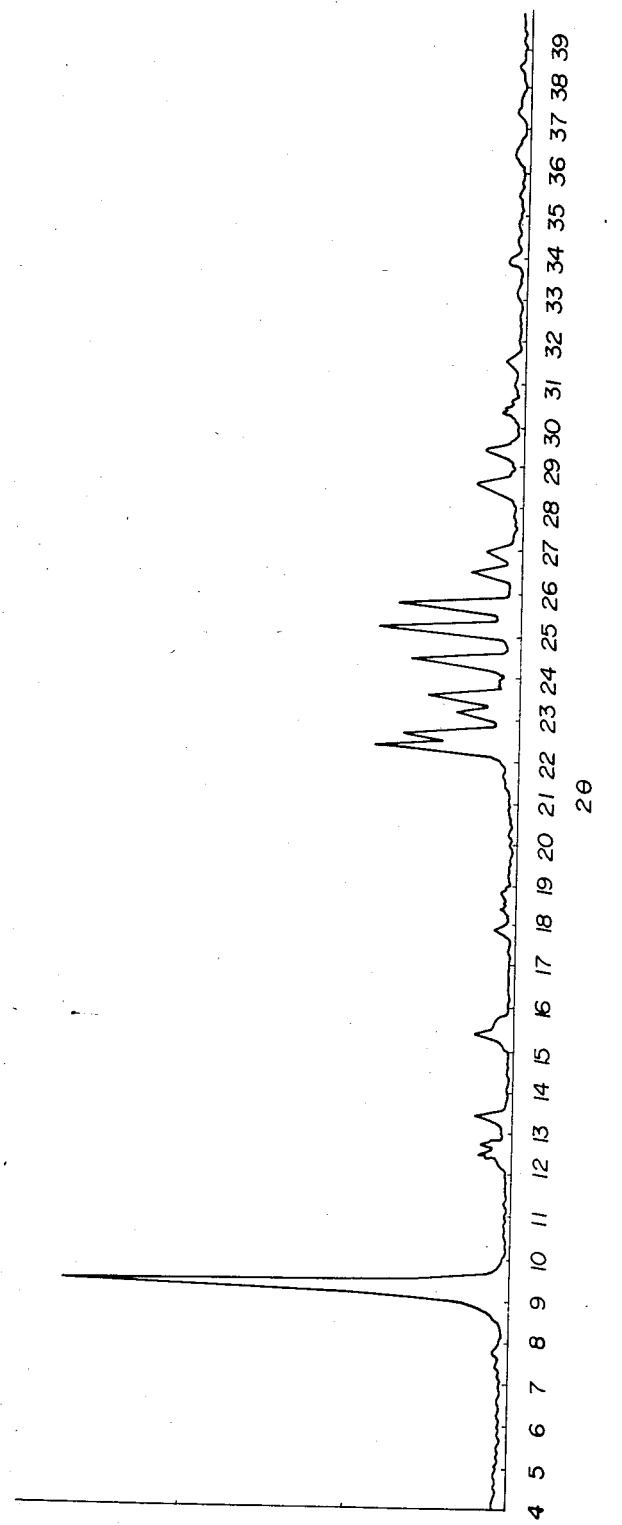

PROCESS FOR PREPARING A CRYSTALLINE ALUMINOSILICATE

BACKGROUND OF THE INVENTION

The present invention relates to: (1) novel crystalline aluminosilicate (hereinafter referred to as "crystalline aluminosilicate (ISI-6)"), (2) a process for preparing said crystalline aluminosilicate (ISI-6), (3) a process for producing hydrocarbons from oxygen-containing compounds with crystalline aluminosilicate (ISI-6) as a catalyst, and (4) a process for producing hydrocarbons from synthesis gas in the presence of a catalyst comprising crystalline aluminosilicate (ISI-6) and metals having an ability to reduce carbon monoxide.

A number of crystalline aluminosilicates, natural or synthetic, have heretofore been known and various processes have been proposed to prepare such crystalline aluminosilicates. These crystalline aluminosilicates are usually prepared by subjecting an aqueous mixture consisting of a silica source, an alumina source and an alkali metal source to a hydrothermal reaction.

A process for preparing crystalline aluminosilicate zeolite having a special crystal structure by adding organic compounds exemplified by tetrapropylammonium bromide to the above described aqueous mixture has recently been developed. For example, Japanese Patent Application Laid-Open Nos. 43800/1977 and 134571/1981 disclose that addition of alcohols results in the preparation of ZMS-5 type zeolite and Zeta 1 or 3 type zeolite. U.S. Pat. No. 4,046,859, No. 4,107,195 and No. 4,146,584 disclose that addition of nitrogen-containing compounds results in the formation of ZSM-21 type of ZSM-35 type zeolite. Furthermore, U.S. Pat. No. 4,251,499 describes that ferrierite is prepared by using piperidine or its derivatives.

SUMMARY OF THE INVENTION

As a result of extensive investigations to develop aluminosilicate of novel composition and crystal structure, it has been found that novel crystalline aluminosilicate having a high silica content can be prepared by adding pyridines and oxygen-containing organic compounds, or pyridines and nitrogen-containing organic compounds except pyridines to an aqueous mixture containing a silica source, an alumina source, an alkali metal source, etc. in a predetermined ratio.

This novel crystalline aluminosilicate is called herein "crystalline aluminosilicate (ISI-6)".

The present invention relates to:

(1) a crystalline aluminosilicate having a composition, as determined after being calcined in air at 550° C. and expressed in molar ratio, represented by the formula (I):

$$pM_{2/n}O \cdot Al_2O_3 \cdot qSiO_2 \quad (I)$$

(wherein M is at least one element selected from alkali metals, alkaline earth metals, and a hydrogen atom, n is a valency of M, and p and q are chosen within the ranges of $0.05 \leq p \leq 3.0$ and $5 \leq q \leq 500$) and further having a principal X-ray diffraction pattern shown in Table 1;

(2) a process for preparing a crystalline aluminosilicate having a composition, as determined after being calcined in air at 550° C. and expressed in molar ratio, represented by the formula (I) as described above and further having a principal X-ray diffraction pattern shown in Table 1, which comprises reacting an aqueous mixture containing (a) a silica source, (b) an alumina source, (c) an alkali metal and/or alkaline earth metal source, (d) a pyridine or derivative thereof, and (e) a component selected from the group consisting of (i) an oxygen-containing organic compound and (ii) a nitrogen-containing organic compound other than a pyridine or derivative thereof in the following molar ratios:

silica $(SiO_2)$/alumina $(Al_2O_3) \geq 5$ a pyridine or derivative thereof/silica = 0.01 to 100 component (e)/silica = 0.01 to 100 hydroxyl ion/silica = 0.001 to 0.5 (excluding hydroxyl ions resulting from organic bases)

water/silica = 5 to 1,000 alkali metal and/or alkaline earth metal/silica = 0.01 to 3 at a temperature ranging between 100° and 300° C. till the crystalline aluminosilicate is formed;

(3) a process for producing hydrocarbons which comprises bringing oxygen-containing compounds into contact with the crystalline aluminosilicate as described in (1) above; and (4) a process for producing hydrocarbons which comprises bringing synthesis gas into contact with a catalyst comprising (A) a metal or metal compound having an ability to reduce carbon monoxide and (B) the crystalline aluminosilicate as described in (1) above.

The above numbered inventions are herein referred to as Inventions (1), (2), (3) and (4), respectively.

TABLE 1

| Lattice Spacing (Å) | Relative Intensity (%) |
|---|---|
| 9.44 ± 0.2 | 100 |
| 7.07 ± 0.2 | 4–40 |
| 6.92 ± 0.15 | 4–30 |
| 6.59 ± 0.15 | 4–30 |
| 5.74 ± 0.15 | 4–30 |
| 3.97 ± 0.1 | 20–100 |
| 3.92 ± 0.1 | 20–70 |
| 3.83 ± 0.1 | 5–50 |
| 3.77 ± 0.1 | 5–50 |
| 3.64 ± 0.07 | 20–100 |
| 3.53 ± 0.07 | 20–100 |
| 3.46 ± 0.07 | 20–80 |
| 3.36 ± 0.07 | 4–20 |
| 3.30 ± 0.07 | 4–20 |
| 3.12 ± 0.07 | 4–30 |
| 3.04 ± 0.07 | 4–20 |
| Irradiation: Cu—$K_\alpha$ | Wavelength: 1.5418 Å |

BRIEF DESCRIPTION OF THE DRAWING

The FIGURE is an X-ray diffraction pattern of the crystalline aluminosilicate prepared in Example 1. The symbol $\theta$ represents a glancing angle.

DETAILED DESCRIPTION OF THE INVENTION

Invention (2) will hereinafter be explained in detail.

An aqueous mixture is prepared by adding (a) a silica source, (b) an alumina source, (c) an alkali metal and/or alkaline earth metal source, (d) a pyridine or its derivative, and (e) a component selected from the group consisting of (i) an oxygen-containing organic compound and (ii) a nitrogen-containing organic compound other than component (d) to water and then is allowed to react at elevated temperatures.

The silica source (a) is not subject to any special limitation; for example, powdered silica, silicic acid, colloidal silica, and dissolved silica can be used. Examples of such dissolved silicas include water glass containing 1 to 5 moles of $SiO_2$ per mole of $Na_2O$ or $K_2O$, silicate, and alkali metal silicate.

Various compounds can be used as the alumina source (b), including aluminum sulfate, sodium aluminate, colloidal alumina, and alumina.

The ratio of silica to alumina in the aqueous mixture can be determined appropriately. The molar ratio of silica ($SiO_2$) to alumina ($Al_2O_3$) is at least 5:1, preferably at least 10:1, and most preferably 15:1 to 1,000:1

As the alkali metal and/or alkaline earth metal source (c), various compounds can be used. The alkali metals and the alkaline earth metals include sodium, potassium, lithium, magnesium and barium. The preferred metals are sodium, potassium and lithium. Examples of the alkali metal source include sodium hydroxide and potassium hydroxide. In addition, sodium silicate and sodium aluminate can be used. These compounds serve as both the silica or alumina source and the alkali metal source. Examples of the alkaline earth metal source include calcium nitrate and calcium chloride.

The molar ratio of alkali metal and/or alkaline earth metal to silica is not critical and can be determined appropriately depending on other various conditions. It is usually 0.01:1 to 3:1 and particularly preferably 0.1:1 to 1:1.

The pyridine or its derivative (d) as used herein act mainly as a crystallization agent. Examples of pyridine derivatives include prydinium chloride, methylpyridine, dimethylpyridine, ethylpyridine, trimethylpyridine, and ethylmethylpyridine. The amount of the pyridine or its derivative being used is usually determined so that the molar ratio of pyridine or its derivative (component (d) to silica is 0.01:1 to 100:1 and preferably 0.05:1 to 10:1.

The oxygen-containing organic compound (e) plays an important role in combination with the component (d) in the formation of the desired crystal structure during the process of preparation of the crystalline aluminosilicate. Suitable examples of the oxygen-containing organic compounds (e) include alcohols, such as methanol, ethanol, propanol, n-butanol, and isopropanol, glycols, such as ethylene glycol and propylene glycol, and ethers, such as dimethyl ether and diethyl ether. Particularly preferred are n-propanol, ethylene glycol, and propane diol. In the Invention (2), as the component (e), a nitrogen-containing organic compound other than a pyridine or derivative thereof (hereinafter referred to merely as the "nitrogen-containing organic compound") can be used in place of the oxygen-containing organic compound. Suitable examples of the nitrogen-containing organic compounds include amines such as isopropylamine and morpholine, diamines such as ethylenediamine, propylenediamine, and phenylenediamine, and aminoalcohols such as monoethanolamine, monopropanolamine and diethanolamine. Of these compounds, morpholine, ethylenediamine, monoethanolamine, and monopropanolamine are preferred. The amount of the component (e) used is determined so that the molar ratio of the component (e) to silica is 0.01:1 to 100:1 and preferably 0.05:1 to 10:1.

These components (a), (b), (c), (d) and (e) are added to water in the above described molar ratios to prepare an aqueous mixture which is then subjected to a hydrothermal reaction. The molar ratio of hydroxyl ions to silica in the aqueous mixture is 0.001 to 0.5 and preferably 0.005 to 0.2. In determining this molar ratio, hydroxyl ions resulting from organic bases such as pyridines are excluded.

In the hydrothermal reaction of the aqueous mixture, it is sufficient for the aqueous mixture to be heated under such conditions, temperature and time, as to form the crystalline aluminosilicate (ISI-6). For example, the aqueous mixture is reacted at autogenous-pressure or under pressure at a temperature of 80° to 300° C., preferably 120° to 200° C. for a period of 5 hours to 10 days, preferably 8 hours to 7 days. The reaction is usually performed while stirring the aqueous mixture. The atmosphere may be replaced by inert gas, if necessary. The pH of the aqueous mixture is adjusted to neutral or alkaline.

It is required for the reaction to be performed always in the presence of the component (d) and the component (e). In the absence of the component (d) or the component (e), the desired crystalline aluminosilicate cannot be obtained.

The order in which the above described components are added in the reaction is not critical. According to a preferred embodiment, the silica source (a), the alumina source (b) and the alkali metal and/or alkaline earth metal source (c) are first added to water and then a mixture of the component (d) and the component (e) is added thereto.

After the reaction is completed, the reaction mass is washed with water, dried at about 120° C. and further calcined in air at 550° C., whereupon crystalline aluminosilicate (ISI-6) having a composition represented by the formula (I) as described above and a principal X-ray diffraction pattern shown in Table 1.

The principal X-ray diffraction pattern of crystalline aluminosilicate (ISI-6) of the invention is, as described above, shown in Table 1. Relative intensities at lattice spacings not shown in Table 1 are not critical. In particular, however, an X-ray diffraction pattern as shown in Table 2 is preferred.

TABLE 2

| Lattice Spacing (Å) | Relative Intensity (%) |
|---|---|
| 11.33 ± 0.2 | 0–5 |
| 9.44 ± 0.2 | 100 |
| 7.07 ± 0.2 | 4–40 |
| 6.92 ± 0.15 | 4–30 |
| 6.59 ± 0.15 | 4–30 |
| 5.74 ± 0.15 | 4–30 |
| 5.40 ± 0.15 | 0–5 |
| 4.94 ± 0.15 | 0–5 |
| 4.81 ± 0.15 | 0–5 |
| 4.71 ± 0.15 | 0–20 |
| 3.97 ± 0.1 | 20–100 |
| 3.92 ± 0.1 | 20–70 |
| 3.83 ± 0.1 | 5–50 |
| 3.77 ± 0.1 | 5–50 |
| 3.64 ± 0.07 | 20–100 |
| 3.53 ± 0.07 | 20–100 |
| 3.46 ± 0.07 | 20–80 |
| 3.36 ± 0.07 | 4–20 |
| 3.30 ± 0.07 | 4–20 |
| 3.12 ± 0.07 | 4–30 |
| 3.04 ± 0.07 | 4–20 |
| 2.94 ± 0.07 | 0–5 |
| 2.88 ± 0.07 | 0–5 |
| 2.83 ± 0.07 | 0–5 |
| 2.70 ± 0.05 | 0–5 |
| 2.64 ± 0.05 | 0–5 |
| 2.60 ± 0.05 | 0–5 |
| 2.58 ± 0.05 | 0–5 |
| Irradiation: Cu—$K_\alpha$ | Wavelength: 1.5418 Å |

The relative intensity was determined with the intensity at the lattice spacing of 9.44±0.2 Å as 100%.

Crystalline aluminosilicate (ISI-6) is silicate having a novel crystal structure and thus can be used in various reactions as a solid acid catalyst or as a catalyst support. In particular, it can be used effectively as a catalyst for use in the production of hydrocarbons.

Thus, next, Invention (3) will hereinafter be explained in detail.

Liquid hydrocarbons used as a gasoline fuel have heretofore been produced from petroleum. In view of exhaustion of petroleum which is predicted to occur in the future, production of gasoline from feedstocks other than petroleum, such as coal and biomass, is now under investigation. U.S. Pat. No. 4,039,600, for example, discloses a process for producing hydrocarbons by passing methanol or dimethyl ether over ZSM-5 type aluminosilicate. These conventional methods, however, have disadvantages in that the yield of the desired liquid hydrocarbon is not satisfactorily high.

As a result of extensive investigations to develop a process for producing hydrocarbons from oxygen-containing compounds derived from coal, biomass and other various materials in a simplified manner and furthermore in a high conversion over long periods of time, it has been found that hydrocarbons can be produced with high efficiency by the use of the crystalline aluminosilicate (ISI-6) as a catalyst.

Invention (3) is concerned with a process for producing hydrocarbons from oxygen-containing compounds by bringing said oxygen-containing compounds into contact with crystalline aluminosilicate (ISI-6) as a catalyst.

Any oxygen-containing compounds can be used in Invention (3). These oxygen-containing compounds have from 1 to 4 carbon atoms and include alcohols, ethers, aldehydes, and carboxylic acids. Suitable examples are methanol, ethanol, propanol, butanol, dimethyl ether, diethyl ether, acetoaldehyde, propylaldehyde, acetic acid, and propionic acid. An especially preferred one is methanol.

The catalyst used in Invention (3) is, as described above, crystalline aluminosilicate (ISI-6) having a composition, as determined after being calcined in air at 550° C. and expressed in molar ratio, represented by the formula (I) and a principal X-ray diffraction pattern shown in Table 1. This crystalline aluminosilicate is usually used as a proton (H) type silicate, a sodium (Na) type silicate, a potassium (K) type silicate, a lithium (Li) type silicate or a magnesium (Mg) type silicate. The aluminosilicate can be used also as metal ion (for example, Pt, Pd, Ni) exchange type silicate which is prepared by ion exchanging alkali metals, such as sodium, or alkaline earth metals contained therein by various techniques. A particularly suitable example is crystalline aluminosilicate having an X-ray diffraction pattern shown in Table 2.

Contacting the oxygen-containing compound with the above described crystalline aluminosilicate is performed at atmospheric pressure or under pressure at a temperature of 250° to 600° C., preferably 300° to 500° C. at a weight hourly space velocity (WHSV) of 0.1 to 50 per hour, preferably 0.5 to 10 per hour.

In accordance with the process of Invention (3), hydrocarbons, especially olefins having from 2 to 4 carbon atoms can be obtained in high yields from oxygen-containing compounds derived from feedstocks other than petroleum, such as coal and biomass. Thus this can be utilized effectively in the production of feed materials for use in chemical industry.

Next, Invention (4) will hereinafter be explained in detail.

Olefins such as ethylene, propylene and butene, liquid hydrocarbons used as a gasoline fuel, etc. have been usually produced from petroleum. In addition, part of the liquid hydrocarbons has been produced by the Fisher-Tropsch process. In recent years, conversion of synthesis gas into hydrocarbons has received increasing attention because of exhaustion of petroleum in the future. However, conventional catalysts for use in the Fisher-Tropsch process have disadvantages in that a wide variety of hydrocarbons are produced, i.e., its distribution is too broad, and in that n-paraffins are mainly produced and the amounts of olefins and aromatic compounds are small.

Various modified techniques have recently been developed to produce hydrocarbons from synthesis gas. For example, a process for producing hydrocarbons from synthesis gas by the use of a catalyst comprising ZSM-5 type zeolite and a metal or metal compound having an ability to reduce carbon monoxide (see Japanese Patent Application Laid-Open No. 142502/1975), a process for conversion of synthesis gas using crystalline ferrosilicate (see Japanese Patent Application Laid-Open No. 96719/1981), a process for conversion of synthesis gas using a catalyst comprising any one of ruthenium, rhodium and osmium, and ZSM-5 zeolite (see U.S. Pat. No. 4,157,338), a process for conversion of synthesis gas using a mixture of a catalyst composed mainly of chromium and zinc and a crystalline gallosilicate catalyst (see Japanese Patent Application Laid-Open No. 16427/1981), and a process for producing hydrocarbons by once converting synthesis gas into alcohols and then the alcohols into the hydrocarbons (see Japanese Patent Application Laid-Open No. 151786/1981) are known. These processes, however, are not yet satisfactory in that expensive raw materials are required in the preparation of the catalysts and the yields and types of hydrocarbons formed are not sufficiently satisfactory.

As a result of extensive investigations to develop a process for producing useful hydrocarbons from synthesis gas in a simplified manner and in high conversions over long periods of time, it has been found that the object is attained by using a catalyst comprising the above described crystalline aluminosilicate (ISI-6) and a specific metal or metal compound.

Invention (4) is concerned with a process for producing hydrocarbons from synthesis gas in the presence of a catalyst, which is characterized in that the catalyst comprises (A) a metal or metal compound having an ability to reduce carbon monoxide and (B) crystalline aluminosilicate having a composition, as determined after being calcined in air at 550° C. and expressed in molar ratio, represented by the formula (I) and having a principal X-ray diffraction pattern shown in Table 1.

The catalyst used in the process of Invention (4) comprises the above described components (A) and (B). As the component (A), metal or metal compound having an ability to reduce carbon monoxide, various compounds can be used. Metals which can be used inclue transition metals, i.e., the metals belonging to Groups IB, IIB, IIIB, IVB, VB, VIB, VIIB and VIII of the Periodic Table. These metals can be used singly or in combination with each other. Suitable examples are iron, nickel, cobalt, chromium, copper, and zinc. Particularly preferred are iron, nickel and cobalt. Metal compounds which can be used include the oxides, carbides, and nitrides of the above described metals, and reduced iron. These metals or metal compounds can be used appropriately. Furthermore, they can be used in combination with other compounds. In addition, as the component (A), the known catalysts, such as a Fisher-Tropsch catalyst, a catalyst for use in preparation of methanol, and a catalyst for use in preparation of higher alcohols, can be used. Suitable examples are nickel or cobalt-base catalysts, such as Ni—MnO—Al$_2$O$_3$—diatomaceous earth and Co—ThO$_2$—MgO—diatomaceous earth, iron-base catalysts, such as Fe—K$_2$O—Al$_2$O$_3$, and CuO—ZnO, ZnO—Cr$_2$O$_3$—CuO, ZnO—Cr$_2$O$_3$, and K$_2$O—Cu—ZnO—Cr$_2$O$_3$.

The component (B) of the catalyst for use in the process of Invention (4) is crystalline aluminosilicate (ISI-6). This crystalline aluminosilicate may contain alkali metals, such as sodium, potassium and lithium, and alkaline earth metals, such as calcium and magnesium, and can be used also as H type silicate. The aluminosilicate can be used also as metal ion (for example, Pt, Pd, Ni) exchange type silicate which is prepared by ion exchanging alkali metals or alkaline earth metals contained therein by various techniques. A particularly suitable example is crystalline aluminosilicate having an X-ray diffraction pattern shown in Table 2.

The ratio of component (A) to component (B) is not critical and can be determined appropriately depending on the type of each component, the type of hydrocarbon to be produced, the reaction conditions, etc. The weight ratio of component (A) to component (B) is usually from 0.001 to 0.99, preferably from 0.01 to 0.8. The components (A) and (B) can be mixed in various manners; for example, they are pelletized and then mixed, or they are powdered and mixed in the form of powder and, thereafter, pelletized, or crystalline aluminosilicate, component (B), is impregnated with a solution of the metal compound, component (A), to deposit the component (A) on the component (B).

In the process of Invention (4), synthesis gas, i.e., a mixture of carbon monoxide and hydrogen, is contacted with the above prepared catalyst to produce hydrocarbons with high efficiency. Usually, the synthesis gas is brought into contact with the catalyst at a temperature of 150° to 500° C., preferably 200° to 400° C. under a pressure of 0 to 150 kilograms per square centimeter (gauge), preferably 10 to 100 kilograms per square centimeter (gauge) at a weight hourly space velocity (WHSV) of 0.1 to 50 per hour, preferably 0.3 to 15 per hour. This contact reaction can be carried out by a batch process. Usually, however, it is preferably performed by a flow process. The process of Invention (4) produces advantages in that the reaction proceeds efficiently under relatively mild conditions, the conversion of synthesis gas is high, and in that the yield of hydrocarbons, particularly C$_5$+ hydrocarbons is high.

The following examples are given to illustrate the present invention in greater detail.

EXAMPLE 1

Solution A

Aluminum sulfate (18 hydrate): 7.52 grams
Concentrated sulfuric acid (97%): 17.6 grams
Water: 100 milliliters Solution B Water glass (SiO$_2$: 29.0% by weight; Na$_2$O; 9.4% by weight; water: 61.6% by weight): 211.0 grams
Water: 96 milliliters Solution C Water: 50 milliliters Solution D Pyridine: 188 milliliters
Ethylene glycol: 188 milliliters Solutions A and B were gradually added dropwise at the same time to Solution C and mixed and, thereafter, the resulting mixture was adjusted to pH 8.5 by adding 13 grams of sulfuric acid (50%). Then, Solution D was added to the mixture, and the ratios of the components were as follows:

silica/alumina = 90 (by mole)
pyridine/silica = 2.3 (by mole)
ethylene glycol/silica = 3.3 (by mole)
hydroxyl ion/silica = 0.09 (by mole)

The above prepared mixture was transferred to a 1-liter autoclave and reacted with stirring at 170° C. under autogenous-pressure for 20 hours.

The reaction mixture was cooled and then washed five times with 1.5 liters of water. Then the mixture was filtered to separate solids, and the solids were dried at 120° C. for 60 hours to obtain 57.0 grams of crystalline silicate (ISI-6) of 100% purity. An X-ray diffraction pattern of the product is shown in FIG. 1. The composition of the product, as determined after being calcined in air at 550° C., was 0.86Na$_2$O.Al$_2$O$_3$.71.4SiO$_2$.

EXAMPLE 2

The procedure of Example 1 was repeated wherein the formulation of Solution D was changed as follows:

Solution D

Pyridine: 188 milliliters
Monoethanolamine: 188 milliliters
The ratios of the components were as follows:
silica/alumina = 90 (by mole)
pyridine/silica = 2.3 (by mole)
monoethanolamine/silica = 3.1 (by mole)

In this way, 56.2 grams of crystalline aluminosilicate (ISI-6) of 100% purity was obtained. The composition of the crystalline aluminosilicate, as determined in the same manner as in Example 1, was 0.31Na$_2$O.Al$_2$O$_3$.73.1SiO$_2$.

EXAMPLE 3

The procedure of Example 1 was repeated wherein the formulation of Solution D was changed as follows:

Solution D

Pyridine: 188 milliliters
Morpholine: 188 milliliters
The ratios of the components were as follows:
silica/alumina = 90 (by mole)
pyridine/silica = 2.3 (by mole)
morpholine/silica = 2.1 (by mole)

In this way, 58.2 grams of crystalline aluminosilicate (ISI-6) of 100% purity was obtained. The composition of the aluminosilicate, as determined in the same manner as in Example 1, was 0.72Na$_2$O.Al$_2$O$_3$.70.5SiO$_2$.

EXAMPLE 4

The procedure of Example 1 was repeated wherein the formulation of Solution D was changed as follows:

Solution D

Pyridine: 188 milliliters n-Propanol: 188 milliliters
The ratios of the components were as follows:
  silica/alumina=90 (by mole)
  pyridine/silica=2.3 (by mole)
  n-propanol/silica=2.5 (by mole)
In this way, 58.1 grams of crystalline aluminosilicate (ISI-6) of 85% purity was obtained. It contained 15% of an impurity, crystalline silicate of different crystal structure. The composition of the aluminosilicate, as determined in the same manner as in Example 1, was $1.01Na_2O.Al_2O_3.68.0SiO_2$.

EXAMPLE 5

The procedure of Example 1 was repeated wherein the formulation of Solution D was changed as follows:

Solution D

Pyridine: 188 milliliters
Ethylenediamine: 188 milliliters
The ratios of the components were as follows:
  silica/alumina=90 (by mole)
  pyridine/silica=2.3 (by mole)
  ethylenediamine/silica=2.7 (by mole)
In this way, 57.5 grams of crystalline aluminosilicate (ISI-6) of 100% purity was obtained. The composition of the aluminosilicate, as determined in the same manner as in Example 1, was $0.33Na_2O.Al_2O_3.72.1SiO_2$.

EXAMPLE 6

The procedure of Example 1 was repeated wherein the formulation of Solution A was changed as follows:

Solution A

Aluminum sulfate (18 hydrate): 33.8 grams
Concentrated sulfuric acid (97%): 2.0 grams
Water: 100 milliliters
The ratios of the components were as follows:
  silica/alumina=20 (by mole)
  pyridine/silica=2.3 (by mole)
  ethylene glycol/silica=3.3 (by mole)
In this way, 65.5 grams of crystalline aluminosilicate (ISI-6) of 100% purity was obtained. The composition of the aluminosilicate, as determined in the same manner as in Example 1, was $0.56Na_2O.Al_2O_3.19.2SiO_2$.

EXAMPLE 7

The procedure of Example 1 was repeated wherein the formulation of Solution A was changed as follows:

Solution A

Aluminum sulfate: 3.37 grams
Concentrated sulfuric acid (97%): 17.6 grams
Water: 100 milliliters
The ratios of the components were as follows:
  silica/alumina=200 (by mole)
  pyridine/silica=2.3 (by mole)
  ethylene glycol/silica=3.3 (by mole)
In this way, 55.8 grams of crystalline aluminosilicate (ISI-6) of 100% purity was obtained. The composition of the aluminosilicate, as determined in the same manner as in Example 1, was $1.13Na_2O.Al_2O_3.156.1SiO_2$.

EXAMPLE 8

The procedure of Example 1 was repeated wherein the formulation of Solution D was changed as follows:

Solution D

Pyridine: 8.1 milliliters
Ethylene glycol: 5.7 milliliters
The ratios of the components were as follows:
  silica/alumina=90 (by mole)
  pyridine/silica=0.1 (by mole)
  ethylene glycol/silica=0.1 (by mole)
In this way, 57.6 grams of crystalline aluminosilicates (ISI-6) of about 90% purity was obtained. It contained small amounts of cristobalite and amorphous substances. The composition of the aluminosilicate, as determined in the same manner as in Example 1, was $0.96Na_2O.Al_2O_3.68.5SiO_2$.

EXAMPLE 9

The procedure of Example 1 was repeated wherein the formulation of Solution D was changed as follows:

Solution D

Pyridinium chloride: 11.6 grams
Ethylene glycol: 47 milliliters
The ratios of the components were as follows:
  silica/alumina=90 (by mole)
  pyridium chloride/silica=0.1 (by mole)
  ethylene glycol/silica=0.1 (by mole)
In this way, 59.5 grams of crystalline aluminosilicate (ISI-6) of about 90% purity was obtained. It contained 10% of amorphous substances. The composition of the aluminosilicate, as determined in the same manner as in Example 1, was $0.92Na_2O.Al_2O_3.70.3SiO_2$.

EXAMPLE 10

The procedure of Example 1 was repeated wherein the formulation of Solution A was changed as follows:

Solution A

Aluminum sulfate: 1.35 grams
Concentrated sulfuric acid (97%): 17.6 grams
Water: 100 milliliters
The ratios of the components were as follows:
  silica/alumina=500 (by mole)
  pyridine/silica=2.3 (by mole)
  ethylene glycol/silica=3.3 (by mole)
In this way, 58.0 grams of crystalline aluminosilicate (ISI-6) of about 80% purity was obtained. It contained 20% of other zeolites.

COMPARATIVE EXAMPLE 1

The procedure of Example 1 was repeated wherein the formulation of Solution D was changed as follows:

Solution D

Ethylene glycol: 188 milliliters
The ratios of the components were as follows:
  silica/alumina=90 (by mole)
  ethylene glycol/silica=3.3 (by mole)
In this case, however, the desired crystalline aluminosilicate was not obtained at all, and 56.0 grams of other crystalline aluminosilicate (ISI-4) of 100% purity was obtained.

EXAMPLE 11

A mixture of crystalline aluminosilicate (ISI-6) as obtained in Example 1 and alumina sol was extrusion molded, and calcined in air at 550° C. for 6 hours. The mold (alumina content: 35% by weight) (2.5 grams) was charged to a flow type reactor through which methanol was passed. In this way, methanol was contacted with the crystalline aluminosilicate (ISI-6) at 370° C. under atmospheric pressure at a weight hourly space velocity (WHSV) of 2.2 per hour. The results are shown in Table 3.

COMPARATIVE EXAMPLE 2

Crystalline aluminosilicate zeolite ZSM-34 (prepared by the method of Example 1 in Japanese Patent Application Laid-Open No. 58499/1978) (2.5 grams) was charged to a flow type reactor through which methanol was passed. In this way, methanol was contacted with the crystalline aluminosilicate zeolite ZSM-34 at 371.1° C. under atmospheric pressure at a weight hourly space velocity (WHSV) of 3.0 per hour. The results are shown in Table 3.

EXAMPLE 12

Crystalline aluminosilicate (ISI-6) as obtained in Example 1 was calcined in air at 550° C., and then was ion-exchanged twice at room temperature with 1 normal ammonium nitrate. The amount of ammonium nitrate used herein was 5 milliliters per 1 gram of the crystalline aluminosilicate. After ion-exchange was completed, the obtained ammonium type crystalline aluminosilicate was washed with pure water, dried at 120° C. for 6 hours, and then calcined in air at 550° C. for 6 hours to obtain proton type (H type) crystalline aluminosilicate.

A molton iron catalyst (catalyst for synthesis of ammonia, produced by BASF Co., S6-10RED) (1.25 grams) was mixed with 1.25 grams of H type crystalline aluminosilicate (ISI-6) mold powder as prepared above. The thus prepared mixed catalyst was charged to a flow type reaction tube, reduced with hydrogen at 450° C. under atmospheric pressure for 14 hours, and then activated with synthesis gas (molar ratio of hydrogen to carbon monoxide=2:1) at 250° C. under atmospheric pressure at a weight hourly space velocity (WHSV) of 0.49 per hour for 2 hours. Then, the synthesis gas (molar ratio of hydrogen to carbon monoxide=2:1) was passed therethrough and contacted with the mixed catalyst at 330° C. under a pressure of 20 kilograms per square centimeter (gauge) at a weight hourly space velocity (WHSV) of 1.46 per hour. The results are shown in Table 4.

TABLE 3

| | Example 11 | Comparative Example 2 |
|---|---|---|
| Conversion of Methanol (%) | 93.1 | 85.9 |
| Hydrocarbon Composition (% by weight) | | |
| $C_1$ | 3.3 | 2.3 |
| $C_2$ (Olefin Content) | 16.7 (16.5) | 25.9 (25.9) |
| $C_3$ (Olefin Content) | 13.2 (11.6) | 19.7 (17.6) |

TABLE 3-continued

| | Example 11 | Comparative Example 2 |
|---|---|---|
| $C_4$ (Olefin Content) | 29.2 (22.5) | 7.3 (5.4) |
| $C_5{}^+$ | 37.7 | 45.1 |
| Olefin Selectivity (%) | 50.6 | 48.9 |

TABLE 4

| | Example 12 |
|---|---|
| Conversion of Carbon Monoxide (%) | 98.8 |
| Hydrocarbon Composition (%) | |
| $C_1$ | 16.8 |
| $C_2$ | 11.8 |
| $C_3$ | 15.1 |
| $C_4$ | 13.1 |
| $C_5{}^+$ | 43.1 |

What is claimed is:

1. A process for preparing a crystalline aluminosilicate which has a composition represented by the general formula after being calcined in air at 500° C. as follows:

$$pM_{2/n}O \cdot Al_2O_3 \cdot qSiO_2$$

wherein M represents at least one element selected from hydrogen, alkali metals, and alkaline earth metals, n represents the valence of M, and p and q each represent a molar ratio and are chosen within the ranges of $0.5 \leq p \leq 3.0$ and $5 \leq q \leq 500$, and has the X-ray diffraction patern set forth in Table 2 which comprises reacting an aqueous mixture containing (a) a silica source, (b) an alumina source, (c) an alkali metal and/or alkaline earth metal source, (d) at least one pyridine compound selected from the group consisting of pyridine, pyridinium chloride, methylpyridine, dimethylpyridine, ethylpyridine, trimethylpyridine and ethylmethylpyridine, and (e) at least one compound selected from the group consisting of methanol, ethanol, propanol, n-butanol, isopropanol, ethylene glycol, propylene glycol, dimethyl ether, diethyl ether, isopropylamine, morpholine, ethylenediamine, propylenediamine, phenylenediamine, monoethanolamine, monopropanolamine and diethanolamine, in the following ratios:

silica ($SiO_2$)/alumina ($Al_2O_3$) $\geq 5$
pyridine compound/silica = 0.01 to 100
component (e)/silica = 0.01 to 100
hydroxyl ion/silica = 0.001 to 0.5 (excluding hydroxyl ions resulting from organic bases)
water/silica = 5 to 1,000
alkali metal and/or alkaline earth metal/silica = 0.01 to 3 at a temperature ranging between 100° and 300° C. till the crystalline aluminosilicate is formed.

* * * * *